US011257196B2

(12) United States Patent
Kaneko et al.

(10) Patent No.: US 11,257,196 B2
(45) Date of Patent: Feb. 22, 2022

(54) MEDICAL IMAGING APPARATUS, MEDICAL IMAGE PROCESSING DEVICE, AND MEDICAL IMAGE PROCESSING PROGRAM

(71) Applicant: Hitachi, Ltd., Tokyo (JP)

(72) Inventors: Yukio Kaneko, Tokyo (JP); Masahiro Ogino, Tokyo (JP); Yoshimi Noguchi, Tokyo (JP); Yoshitaka Bito, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 77 days.

(21) Appl. No.: 16/804,054

(22) Filed: Feb. 28, 2020

(65) Prior Publication Data

US 2020/0286214 A1 Sep. 10, 2020

(30) Foreign Application Priority Data

Mar. 7, 2019 (JP) .............................. JP2019-041887

(51) Int. Cl.
*G06K 9/00* (2006.01)
*G06T 5/20* (2006.01)
(Continued)

(52) U.S. Cl.
CPC ................. *G06T 5/20* (2013.01); *G06N 3/08* (2013.01); *G06N 20/00* (2019.01); *G06T 5/002* (2013.01);
(Continued)

(58) Field of Classification Search
CPC ............ A61K 2300/00; A61K 31/7115; A61K 2039/505; A61K 2039/55561;
(Continued)

(56) References Cited

U.S. PATENT DOCUMENTS

2016/0012569 A1* 1/2016 Hanada ................. G06T 3/4038
382/131
2018/0240219 A1* 8/2018 Mentl ................... G06T 11/008
(Continued)

OTHER PUBLICATIONS

Isogawa K. et al., "Noise Level Adaptive Deep Convolutional Neural Network for Image Denoising", Proceedings of International Society for Magnetic Resonance in Medicine, 2018, vol. 26, pp. 2797.

*Primary Examiner* — Xin Jia
(74) *Attorney, Agent, or Firm* — Mattingly & Malur, PC

(57) ABSTRACT

Image processing using a machine learning model is enabled, thereby accurately reducing noise to improve image quality. A medical image is acquired; and it is evaluated whether noise in the medical image exceeds a predetermined reference value. A noise reducer reduces the noise of the medical image that has been determined to include noise that exceeds the reference value. The noise of the medical image is reduced using a machine learning model constructed by collecting a plurality of learning data sets that include an image with noise as input data and an image without noise as output data. The machine learning model includes a plurality of layers that perform convolution on an image that is input, one layer of which includes a filter layer in which a plurality of linear or nonlinear filters are incorporated, and convolution coefficients of the plurality of linear or nonlinear filters are predetermined.

12 Claims, 11 Drawing Sheets

(51) Int. Cl.
*G06N 3/08* (2006.01)
*G06N 20/00* (2019.01)
*G06T 5/00* (2006.01)
*G06T 7/00* (2017.01)
*G06T 11/00* (2006.01)
*G16H 30/40* (2018.01)
*G16H 30/20* (2018.01)

(52) U.S. Cl.
CPC .......... *G06T 7/0012* (2013.01); *G06T 11/003* (2013.01); *G16H 30/20* (2018.01); *G16H 30/40* (2018.01); *G06T 2207/10088* (2013.01); *G06T 2207/20081* (2013.01); *G06T 2207/20084* (2013.01); *G06T 2207/20092* (2013.01); *G06T 2207/30004* (2013.01); *G06T 2207/30168* (2013.01); *G06T 2210/41* (2013.01)

(58) Field of Classification Search
CPC ...... A61K 39/39; A61K 39/395; A61K 45/06; A61P 35/00; C07K 14/435; C07K 16/244; C07K 16/2818; C07K 2317/76; G06N 20/00; G06N 3/0454; G06N 3/08; G06T 11/003; G06T 11/008; G06T 2207/10081; G06T 2207/10088; G06T 2207/10132; G06T 2207/20081; G06T 2207/20084; G06T 2207/20092; G06T 2207/30004; G06T 2207/30168; G06T 2210/41; G06T 5/002; G06T 5/20; G06T 7/0012; G16H 30/20; G16H 30/40
See application file for complete search history.

(56) References Cited

U.S. PATENT DOCUMENTS

2019/0209867 A1\* 7/2019 Sun ................ G06K 9/3233
2019/0325621 A1\* 10/2019 Wang ................ A61B 6/037

\* cited by examiner

INPUT IMAGE
(LOW IMAGE QUALITY IMAGE)

OUTPUT IMAGE
(HIGH IMAGE QUALITY IMAGE)

MEDICAL IMAGING APPARATUS, MEDICAL IMAGE PROCESSING DEVICE, AND MEDICAL IMAGE PROCESSING PROGRAM

INCORPORATION BY REFERENCE

The present application claims priority from Japanese patent application JP-2019-41887 filed on Mar. 7, 2019, the content of which is hereby incorporated by reference into this application.

BACKGROUND OF THE INVENTION

Field of the Invention

The present invention relates to a medical imaging apparatus that uses a machine learning model, and a medical image processing device and method.

Background Art

Increased image quality is desired for medical images acquired by medical image capturing apparatuses such as MRIs, CTs, and ultrasonic imaging apparatuses in order to prevent lesions and diseases from being overlooked. It is required to reconstruct images with a small amount of measurement data in order to shorten the imaging time in MRIs, reduce exposure in CTs, and achieve high frame rate imaging in ultrasonic imaging apparatuses. However, using only a small amount of measurement data cause the degradation of image quality. There have been proposed methods for increasing image quality and, in particular, reducing noise. Examples of them include the following methods:

(1) Selectively using a plurality of types of linear or nonlinear image filters. Specifically, reducing noise by performing filter convolution processing on images that include noise using linear or nonlinear filters that are effective for reducing noise. Examples of such filters include smoothing filters, average filters, and bilateral filters.

(2) Repeatedly performing correction processing to reduce noise components (iterative reconstruction).

(3) Reducing noise using a machine learning model generated by collecting a learning set consisting of image data with noise (input data set) and image data without noise (output data set) (ISOGAWA K. et al., NOISE LEVEL ADAPTIVE DEEP CONVOLUTIONAL NEURAL NETWORK FOR IMAGE DENOISING, PROCEEINGS OF INTERNATIONAL SOCIETY FOR MAGNETIC RESONANCE IN MEDICINE, 2018, vol. 26, p. 2797).

SUMMARY OF THE INVENTION

However, when using linear or nonlinear filters, filters that are suitable for reducing noise in a particular image are individually selected on the basis of the experience of the designer. Consequently, there are differences in the noise reduction effects that are obtained. It is possible to combine multiple stages of filters, but there are countless patterns in which the plurality of filters can be combined. As such, depending on the combination, optimization may be difficult. For example, the noise reducing effect may be insufficient or there may be failures such as image blurring due to the excessive application of a filter.

When reducing noise by iterative reconstruction, correction processing is repeatedly carried out and, as such, the time needed for calculation is enormous.

Furthermore, while there is a potential for obtaining higher noise reduction effects when increasing image quality using machine learning than when increasing image quality using conventional filters or the like, there may be cases in which the noise cannot be decreased for certain. Specifically, the processing in machine learning is, in principle, carried out in a black box, and it is difficult to analyze the type of processing that is being performed. In such processing, non-noise components may be incorrectly determined as noise and inappropriate image processing may be carried out.

However, since the processing is carried out in a black box, it is difficult to even analyze if the image processing was inappropriate. Due to this, in the case of medical images, for example, it is possible that a lesion may be incorrectly determined as noise, and the possibility of such incorrect determinations is an obstacle to the use of machine learning in medical settings.

In light of the foregoing, an object of the present invention is to make the image processing content in image processing using a machine learning model performed in a white box, to the extent possible, and capable of being analyzed, thereby preventing inappropriate image processing and accurately reducing noise to improve image quality.

The present invention provides the following means to solve the problems described above.

One aspect of the present invention is a medical imaging apparatus that includes an imaging device that acquires a medical image, and an image processor that carries out convolution processing on the medical image. The image processor includes a storage unit that stores a plurality of sets of predetermined convolution coefficients and a weighting factor of each of the sets of convolution coefficients, and a calculation unit that carries out calculation of the convolution processing using the sets of convolution coefficients and the weighting factors thereof that are stored in the storage unit. Image quality is improved by the convolution processing.

Another aspect of the present invention is a medical image processing device that includes a medical image acquirer that acquires a medical image, an image processor that carries out convolution processing on the medical image, a storage unit that stores a plurality of sets of predetermined convolution coefficients and a weighting factor of each of the sets of convolution coefficients, and a calculation unit that carries out calculation of the convolution processing. The storage unit includes a plurality of sets of convolution coefficients calculated by a learning model that includes a plurality of layers, the learning model being learned on the basis of a data set that includes a high-noise image as input data and low-noise image as output data. One layer of the learning model includes a filter layer in which a plurality of predetermined linear or nonlinear filters is incorporated. Image quality is improved by the convolution processing.

Another aspect of the present invention is a medical image processing program that causes a computer to execute the following steps: a medical image acquiring step of acquiring a medical image, a noise evaluation step to evaluate whether noise in the medical image exceeds a predetermined reference value; and, for the medical image that has been determined, by the noise evaluator, to include noise that exceeds the reference value, a step of reducing the noise of the medical image using a machine learning model constructed by collecting a plurality of learning data sets that include an image that includes noise as input data and an image that does not include noise as output data, the machine learning model including a plurality of layers that carry out convolution processing on an image that is input, one layer of the plurality of layers including a filter layer in which a plurality of linear or nonlinear filters are incorporated, convolution coefficients of the plurality of linear or nonlinear filters being predetermined.

Another aspect of the present invention is a machine learning model constructed by collecting a plurality of learning data sets that include an image with noise as input data and an image without noise as output data. The machine learning model includes a plurality of layers that carry out convolution processing on an image that is input, wherein one layer of the plurality of layers includes a filter layer in which a plurality of linear or nonlinear filters are incorporated, convolution coefficients of the plurality of linear or nonlinear filters being predetermined.

According to the present invention, analysis of the image processing content in image processing using a machine learning model is enabled, thereby making it possible to prevent inappropriate image processing and accurately reduce noise to improve image quality.

DETAILED DESCRIPTION OF THE INVENTION

Figure 1:
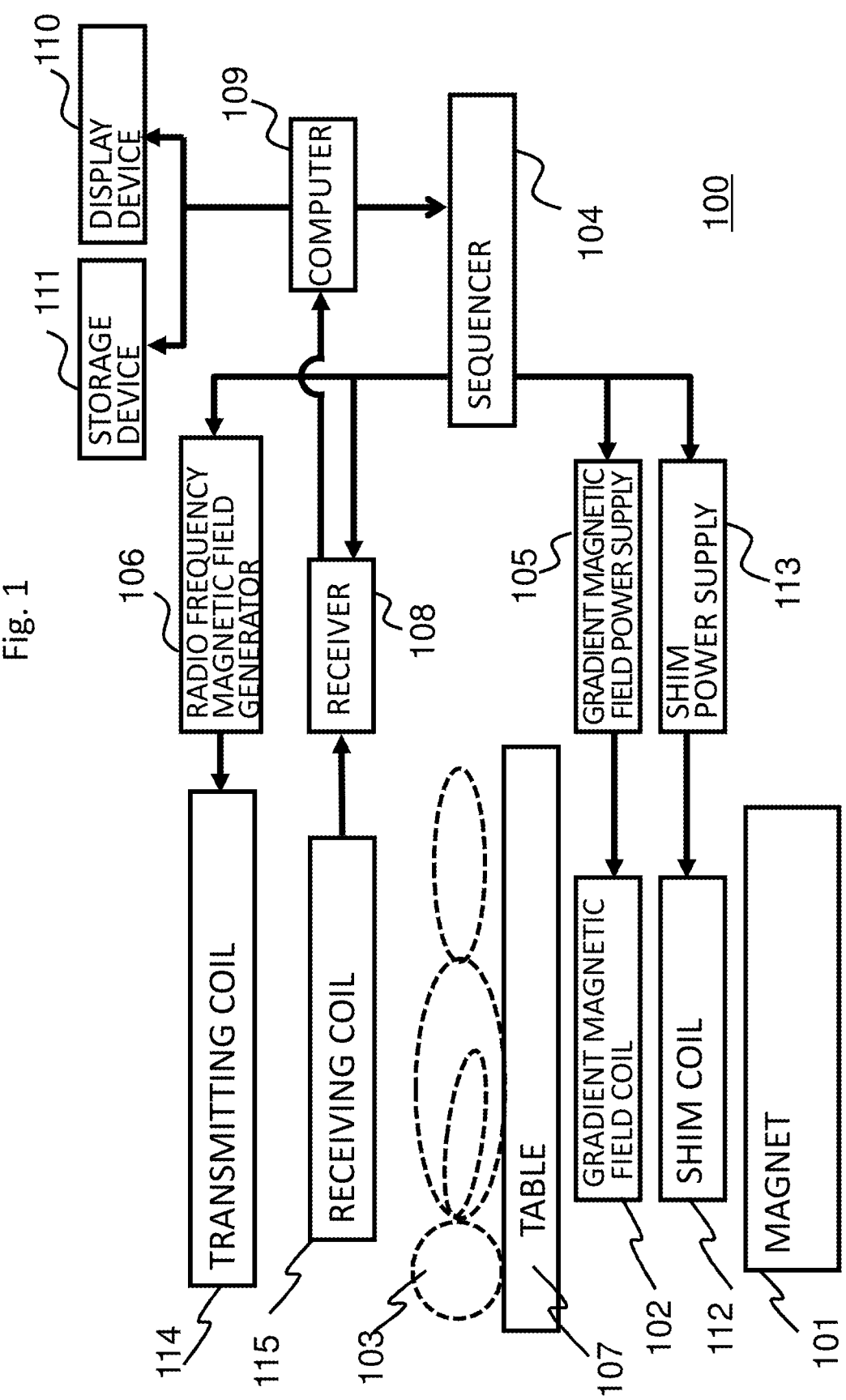
FIG. 1 is a drawing illustrating an overview of a medical imaging apparatus (an MRI apparatus) according to Embodiment 1.

Hereinafter, embodiments in which the machine learning model of the present invention is applied to medical imaging apparatuses are described. The machine learning model of the present invention is constructed by collecting a plurality of learning data sets consisting of images that include noise as input data and images that do not include noise as output data. The machine learning model includes a plurality of layers that perform convolution on an inputted image. One layer of the plurality of layers includes a filter layer in which a plurality of linear or nonlinear filters is incorporated. The convolution coefficients of the plurality of linear or nonlinear filters are predetermined.

Embodiment 1

Next, an embodiment in which the present invention is applied to a nuclear magnetic resonance imaging apparatus is described.

Note that, in all of the drawings provided for explaining each of the embodiments, components with identical functions are marked with the same reference numerals, and redundant explanation thereof is foregone. It should be noted that this does not limit the present invention.

First, the overall structure of an MRI apparatus according to the present embodiment will be described. FIG. 1 is a block diagram of an MRI apparatus 100 according to the present embodiment. As illustrated in FIG. 1, the MRI apparatus 100 according to the present embodiment includes a magnet 101 that generates a static magnetic field, a coil (gradient magnetic field coil) 102 that generates a gradient magnetic field, a shim coil 112 that adjusts static magnetic field uniformity, a sequencer 104, an RF transmitting coil (transmitting coil) 114 that irradiates (transmits) a radio frequency magnetic field, an RF receiving coil (receiving coil) 115 that detects (receives) nuclear magnetic resonance signals generated from a subject 103, a table 107 on which the subject 103 is placed, a gradient magnetic field power supply 105, a radio frequency magnetic field generator 106, a receiver 108, a shim power supply 113, and a computer 109 that controls the various components of the MRI apparatus 100 to realize imaging.

The gradient magnetic field coil 102 and the shim coil 112 are respectively connected to the gradient magnetic field power supply 105 and the shim power supply 113. The transmitting coil 114 and the receiving coil 115 are respectively connected to the radio frequency magnetic field generator 106 and the receiver 108.

In accordance with instructions from the computer 109, the sequencer 104 sends commands to the gradient magnetic field power supply 105, the shim power supply 113, and the radio frequency magnetic field generator 106, thereby causing each to generate a gradient magnetic field and RF. The RF is irradiated (transmitted) on the subject 103 via the transmitting coil 114. The nuclear magnetic resonance signals generated from the subject 103 in response to the RF being irradiated are detected (received) by the receiving coil 115, and demodulation is performed by the receiver 108. The computer 109 uses the sequencer 104 to set the magnetic resonance frequency that serves as the basis of the demodulation by the receiver 108. The demodulated signal is sent to the computer 109 via an A/D conversion circuit, and signal processing such as image reconstruction is carried out. The results of that processing are displayed on a display device 110 that is connected to the computer 109. The demodulated signal, measurement conditions, and the like are, as desired, saved in a storage device 111 that is connected to the computer 109.

The MRI apparatus of the present embodiment includes an image processor 200 that uses a machine learning model to carry out noise reduction processing on reconstructed images created by the computer 109. The image processor 200 can be provided in the computer 109 that performs image reconstruction based on echo signals, or can be provided in a computer, other than the computer 109, that functions as an image reconstructer such as, for example, a medical image processing device that is independent from the MRI apparatus. Unless otherwise indicated, the configurations of the components other than the image processor 200, and the actions of the MRI apparatus are the same as those of known MRI apparatuses.

Figure 2:
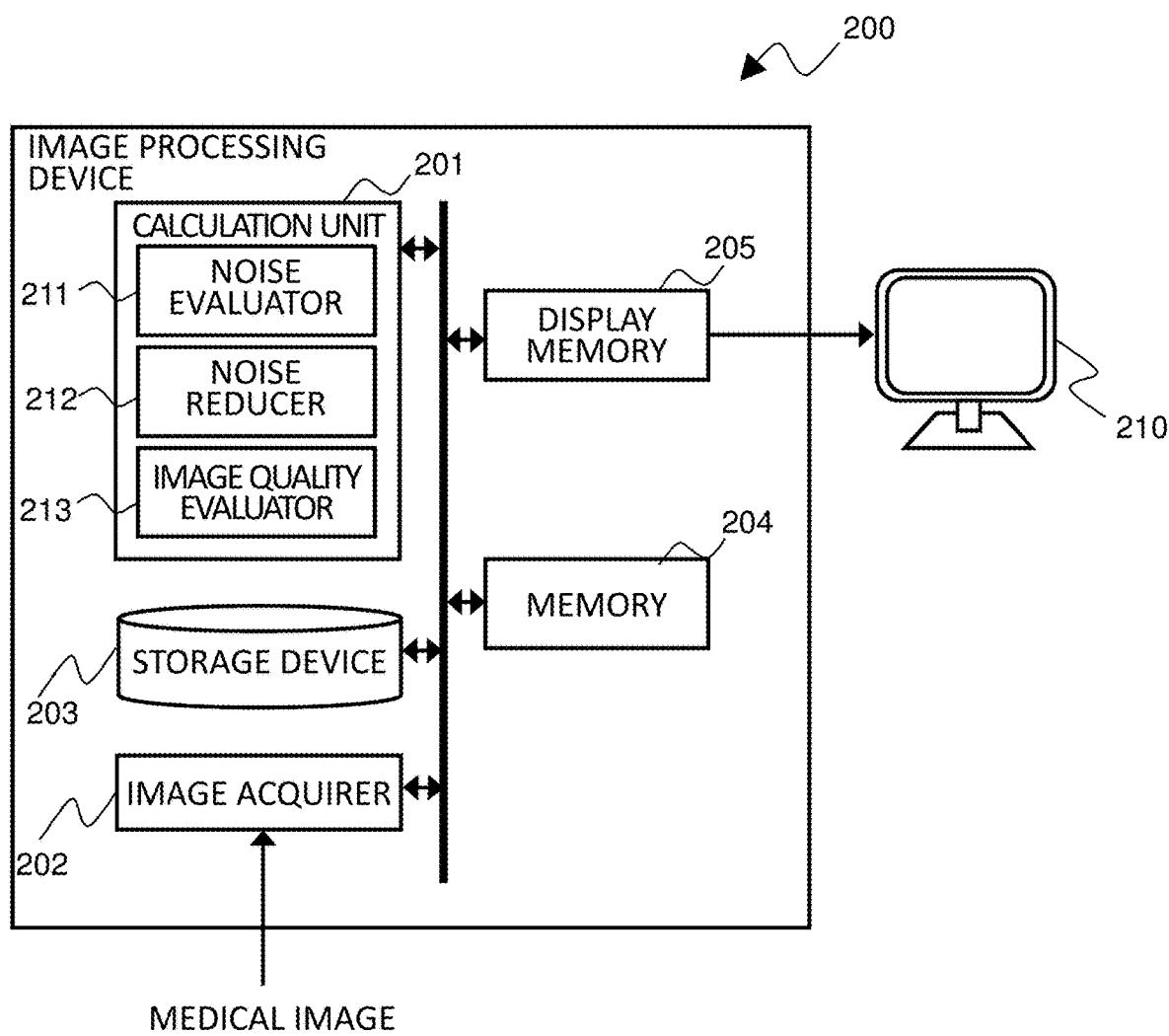
FIG. 2 is a block diagram illustrating a schematic configuration of a medical image processing device (image processor) according to Embodiment 1, to which a machine learning model is applied.

FIG. 2 illustrates a schematic configuration of the image processor 200. In FIG. 2, the configuration of the image processor 200 as a medical image processing device is illustrated, but the configuration is the same when the image processor 200 is provided in the computer 109.

As illustrated in FIG. 2, the image processor 200 includes a calculation unit 201, an image acquirer 202, a storage device 203, a memory 204, and a display memory 205. The image processor 200 carries out desired image processing by acquiring, via the image acquirer 202, a medical image from the image reconstructer of the computer 109. The image processor 200 is connected to a display 210 that displays, via the display memory 205, an image that has been subjected to processing by the image processor 200. In cases in which the image processor 200 is an independent medical image processing device, the image processor 200 is connected to a modality, a medical image database, or the like (not illustrated in the drawings), and acquires the medical image from these databases using the image acquirer 202.

The calculation unit 201 controls the entire image processor 200 and, also, executes predetermined calculation processing for carrying out noise reduction processing on the medical image acquired by the image acquirer 202 (main function as image processor).

Thus, as illustrated in FIG. 2, the calculation unit 201 includes, as a main function, a noise reducer 212. Furthermore, while not essential, the calculation unit 201 may also include functions of a noise evaluator 211 and an image quality evaluator 213. Note that the functions that the calculation unit 201 realizes, namely the noise evaluator 211, the noise reducer 212, and the image quality evaluator 213, can be realized by software by reading and executing a program stored in the memory of the calculation unit 201 or the like.

Note that the calculation unit 201 can include a central processing unit (CPU), a graphics processing unit (GPU), or a combination of a CPU and a GPU. Part or all of the operations executed by the various components of the calculation unit 201 can be realized by an application specific integrated circuit (ASIC) and/or a field-programmable gate array (FPGA).

The noise evaluator 211 evaluates the noise level of the medical image acquired by the image acquirer 202.

Specifically, the noise evaluator 211 compares a noise reference value, which is predetermined for each modality, body part (site), and imaging method of the medical image to be evaluated for noise, with the noise level of that medical image. When the noise exceeds the reference values, the noise evaluator 211 sets that medical image as an image for noise reduction processing. Note that, when the noise evaluator 211 is not provided, the acquired medical image is subjected as acquired to the processing of the noise reducer 212.

Figure 3:
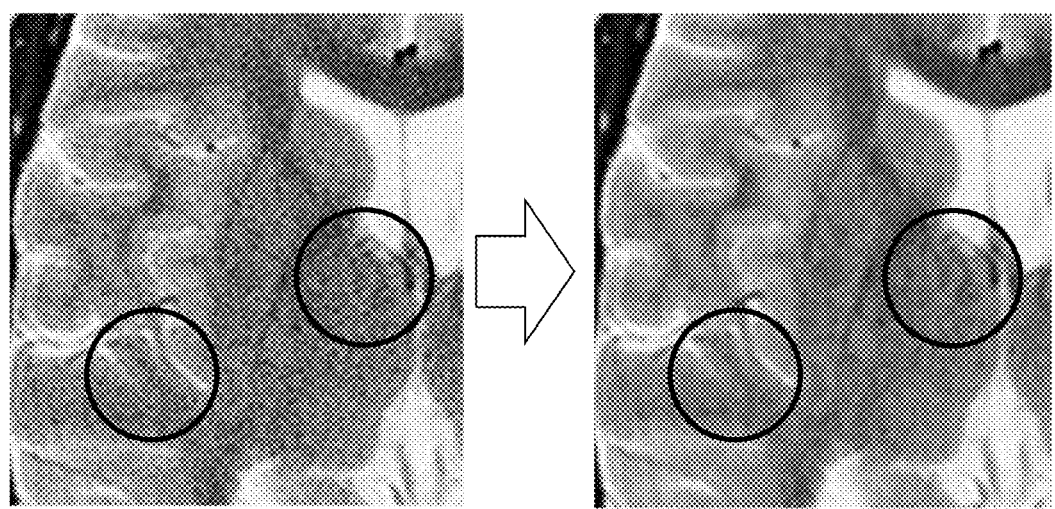
FIG. 3 is a reference drawing illustrating a medical image before and after being subjected to noise reduction in the image processor depicted in FIG. 2.

The noise reducer 212 applies the machine learning model and carries out noise reduction processing for the medical image set as the image for noise reduction processing by the noise evaluator 211. In this case, the machine learning model is an optimized artificial intelligence algorithm, and is a program that has the same functionality as a function that outputs specific data in response to input data. Accordingly, the machine learning model can be stored in the storage device 203. FIG. 3 illustrates, as a reference, images before and after noise reduction. The machine learning model will be described in detail later.

The image quality evaluator 213 evaluates the image quality of the medical image that was subjected to the noise reduction processing by the noise reducer 212. Specifically, the image quality evaluator 213 generates an image processing map that indicates what type of image processing was carried out by the noise reducer 212, and an image quality map that maps an index such as the peak signal-to-noise ratio (PSNR) and the structural similarity (SSIM) for the medical image that was subjected to the noise reduction processing.

The memory 204 stores the programs and the progress of the calculation processing executed by the calculation unit 201.

The storage device 203 stores the noise reference values, which are predetermined for each modality, part, and imaging method of the medical image to be evaluated for noise, used when the noise evaluator 211 carries out noise evaluation and, in addition, programs that are executed by the calculation unit 201 and data required for the execution of these programs. Specifically, the storage device 203 stores a plurality of sets of convolution coefficients that define learned machine learning models (described later) and a weighting factor for each of the convolution coefficients.

Furthermore, the storage device 203 stores the medical image acquired by the image acquirer 202 (in this case, an MR image) and additional information about the medical image. Examples of the additional information include the modality at which the medical image was captured, the imaged part, and the position/posture when imaging. Devices capable of exchanging data with hard disks such as CDs and DVDs, USB memory, SD cards and other portable recording media can be used as the storage device 203.

The display memory 205 temporarily stores display data for displaying an image or the like on the display 210. The display 210 displays the image for which the image processor 200 reduced the noise, and the image map and the imaging processing map generated by the image quality evaluator 213. Thus, the display 210 provides the medical image and the content of the image processing to a user.

Construction of Machine Learning Model

The noise reducer 212 uses the machine learning model to carry out the noise reduction processing. In the present embodiment, a convolution neural network (CNN), for example, is used as the machine learning model for noise reduction, and the image quality is improved by carrying out noise reduction processing on a medical image that includes a comparatively large amount of noise due to being captured in a short amount of time.

Figure 4:
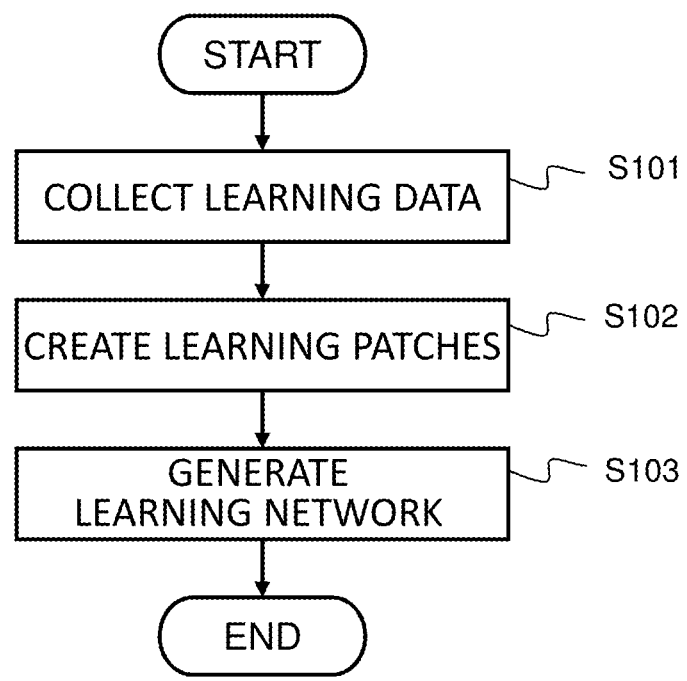
FIG. 4 is a flowchart explaining the processing carried out to construct the machine learning model according to Embodiment 1.

In one example, the machine learning model can be constructed using a dedicated or general use computer, or the like, by following the procedure illustrated in FIG. 4.

As illustrated in FIG. 4, in step S101, learning data, required for learning for noise reduction, is collected. In one example, a plurality of learning data sets consisting of image data with noise and image data without noise (or with a small amount of noise) are collected. Examples of the image data with noise and the image data without noise include sets of undersampling data acquired by thinning out k space and full sampling data acquired without thinning out k space, sets of low resolution data and high resolution data, and the like. Another example is sets of low image quality images acquired by reducing the number of additions when imaging and high image quality images. Other examples include data acquired by varying noise generation conditions.

Next, in step S102, a portion of the image data included in the collected learning data sets is extracted, and learning patches are created. In one example, a plurality of 32×32 patches are created from image data having a size of 512×512. In step S203, all of the learning patches are input, feature quantities are learned, and the machine learning model (noise reduction network) is constructed.

Figure 5:
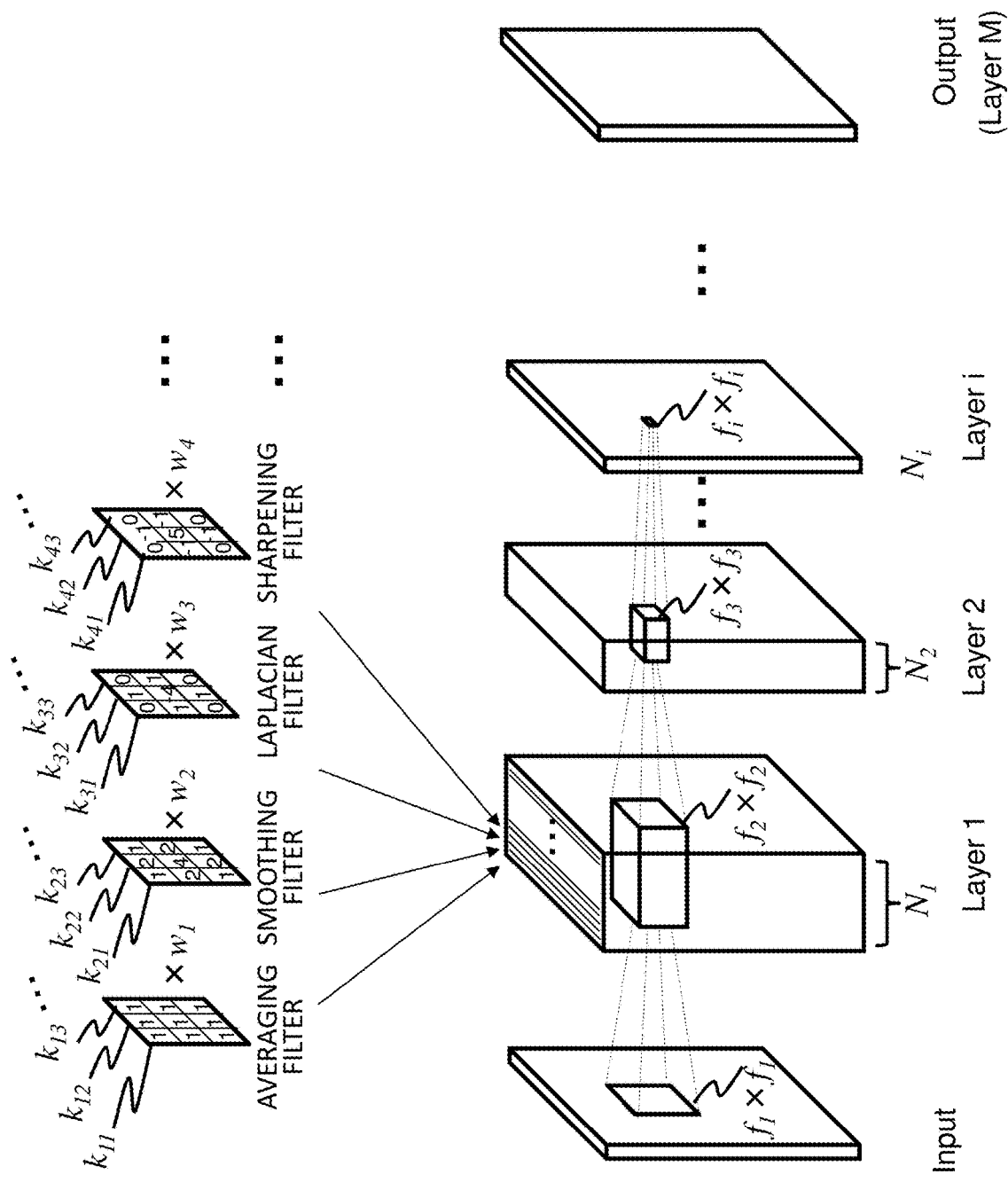
FIG. 5 is a reference drawing for the machine learning model according to Embodiment 1.

The machine learning model generated through this procedure is, as illustrated in FIG. 5, a network consisting of a plurality of convolution layers. In the example illustrated in FIG. 5, the feature quantity extracted at each convolution layer is defined as N1, N2 . . . , the kernel size of the processing target is defined as f1, f2 . . . , the set of convolution coefficients of each kernel is defined as (k11, k12, k13 . . . ), (k21, k22, k23 . . . ) . . . , and the weighting factor of each set of convolution coefficients is defined as w1, w2 . . . . The sets of convolution coefficients and the weighting factor of each set of convolution coefficients of the plurality of convolution layers are stored in the storage device 203 and used in the noise reduction processing.

Each convolution layer of a typical convolution neural network performs processing for condensing feature points from the original image using a filter, and the processing is carried out by randomly assigning an initial value to the kernel. Each convolution layer carries out processing for applying a filter to the original image. These filters are automatically created and change according to the learning. As such, even if the calculated kernel is examined, it is difficult to understand what type of processing is being carried out.

As such, with the machine learning model according to the present embodiment, one layer of an early stage of the plurality of convolution layers is formed so as to be a filter layer, in which a plurality of linear or nonlinear filters having predetermined convolution coefficients, is incorporated. It is preferable that the filter layer is a first layer. Examples of the linear or nonlinear filters to be used in the filter layer include smoothing filters, averaging filters, differential filters, secondary differential filters, Sobel filters, Laplacian filters, and sharpening filters. The weighting of each of these filters is learned and determined by providing a degree of freedom when constructing the machine learning model. After the filter layer, the machine learning model is constructed by providing a degree of freedom to the kernel characteristics and learning. Note that the filters used in the filter layer may be existing filters such as smoothing filters, averaging filters, differential filters, secondary differential filters, Sobel filters, Laplacian filters, and sharpening filters, or may be filters designed by a different method. Additionally, filter layers may be inserted into all of the layers. Furthermore, FIG. 5 illustrates an example in which the network structure is a super resolution CNN (SRCNN), but other network structures, such as U-Net, may be used.

When carrying out the noise reduction using the machine learning model constructed as described above, the filter layer of the early network stage (the first layer) does not consist of filters automatically generated by machine learning, but rather of a plurality of linear or nonlinear filters for which the convolution coefficients are predetermined. As such, it is easy to analyze the type of processing that is being carried out. For example, it is possible to analyze the processing content and discern that, for example, the smoothing filter and the sharpening filter are being respectively applied at ratios of 0.7 and 0.3. In particular, configuring the filter layer as the first layer results in a certain degree of the noise of the input image being reduced at the first layer. As such, it is sufficient that noise reduction, using the filters automatically generated by the machine learning model, be applied only to the remaining noise components.

In the conventional construction of a machine learning model, a large amount of learning data sets must be collected and iterative learning must be performed. In the embodiments of the present invention, however, since the first layer is configured as the filter layer, the amount of learning data sets needed to construct the machine learning model and the calculation costs can be reduced.

Figure 6:
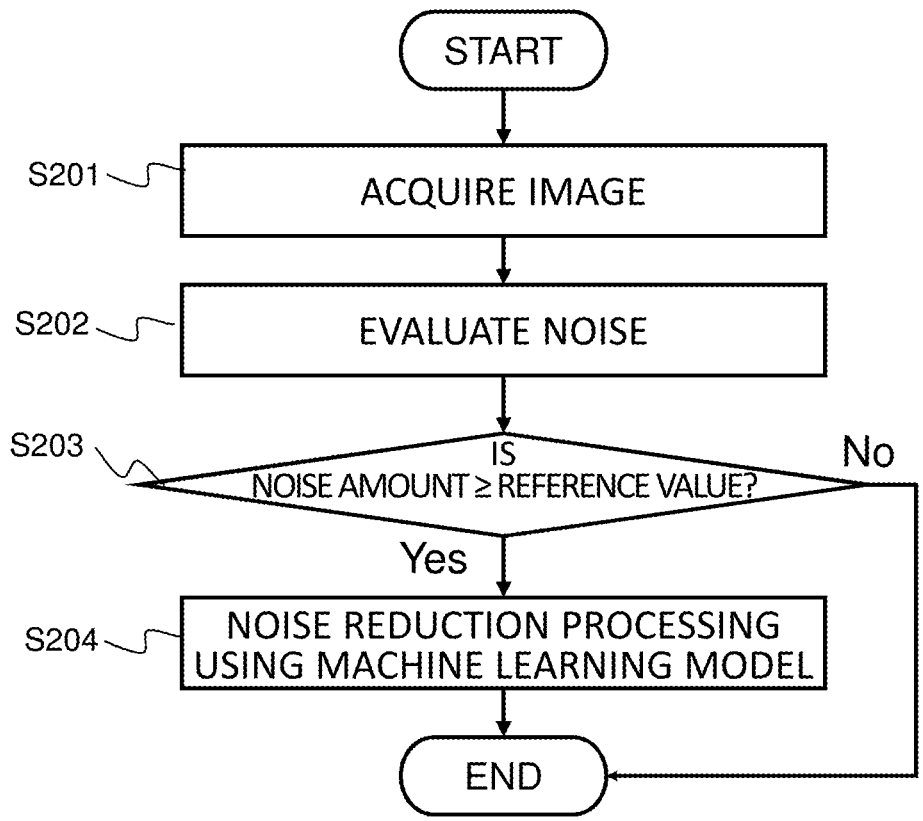
FIG. 6 is a flowchart explaining noise reduction processing according to Embodiment 1.

The noise reduction processing is carried out in the image processor 200 configured as described above, according to the flowchart illustrated in FIG. 6. First, in step S201, a medical image is acquired by the image acquirer 202. Next, in step S202, the noise level of the acquired medical image is evaluated. Standard deviation (SD) or the like can be used to evaluate the noise level.

In step S203, the noise level evaluated in step S202 is compared with the reference value stored in the storage device 203, and it is determined whether the noise level of the medical image exceeds the reference value. In the determination in step S203, when the noise level of the medical image exceeds the reference value, step S204 is executed and the noise reduction processing using the machine learning model is carried out. In the determination in step S203, when the noise level of the medical image is less than the reference value, the processing is ended without carrying out the noise reduction processing.

The image that was subjected to the noise reduction processing can be displayed on the display 201 via the display memory 205. At this time, the image quality evaluator 213 generates an image processing map and/or an image quality map for the medical image that was subjected to the noise reduction processing, and outputs the generated image processing map and/or image quality map to the display memory 205. The display 210 can display, on the display 210, the image processing map and the image quality map alone or together with the medical image that was subjected to the noise reduction processing.

Figure 7:
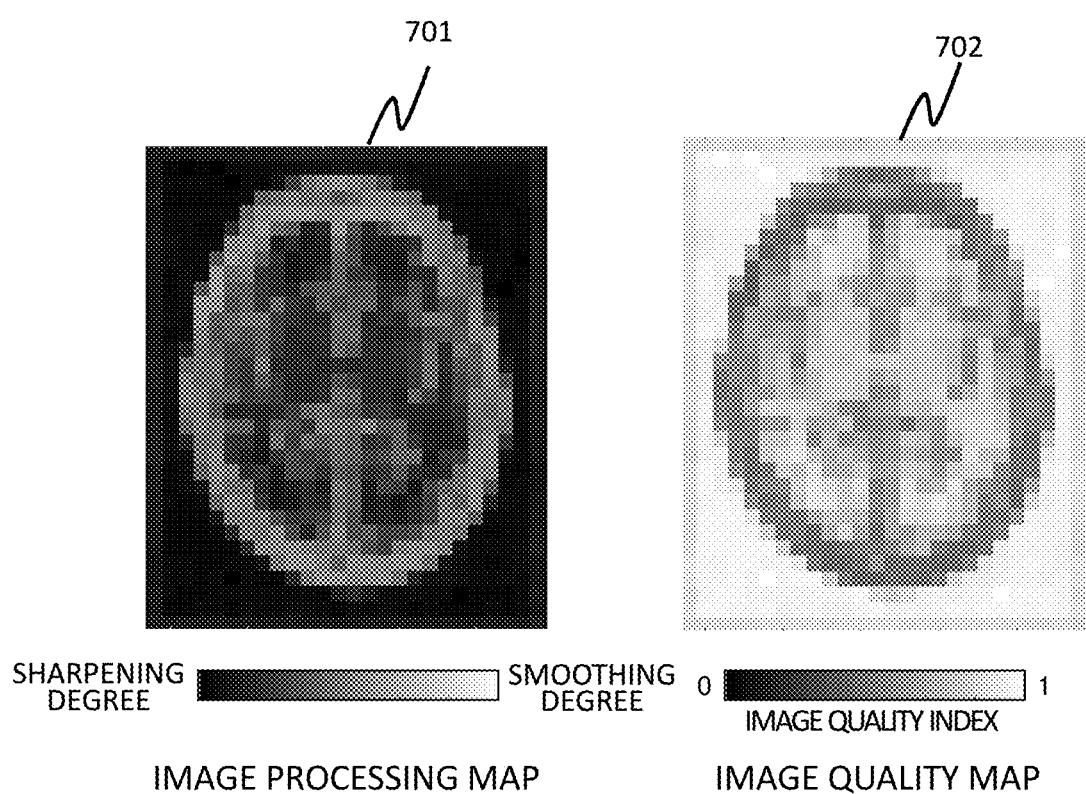
FIG. 7 is a drawing illustrating a display example of the results of the noise reduction processing carried out by the image processor depicted in FIG. 2.
Figure 8:
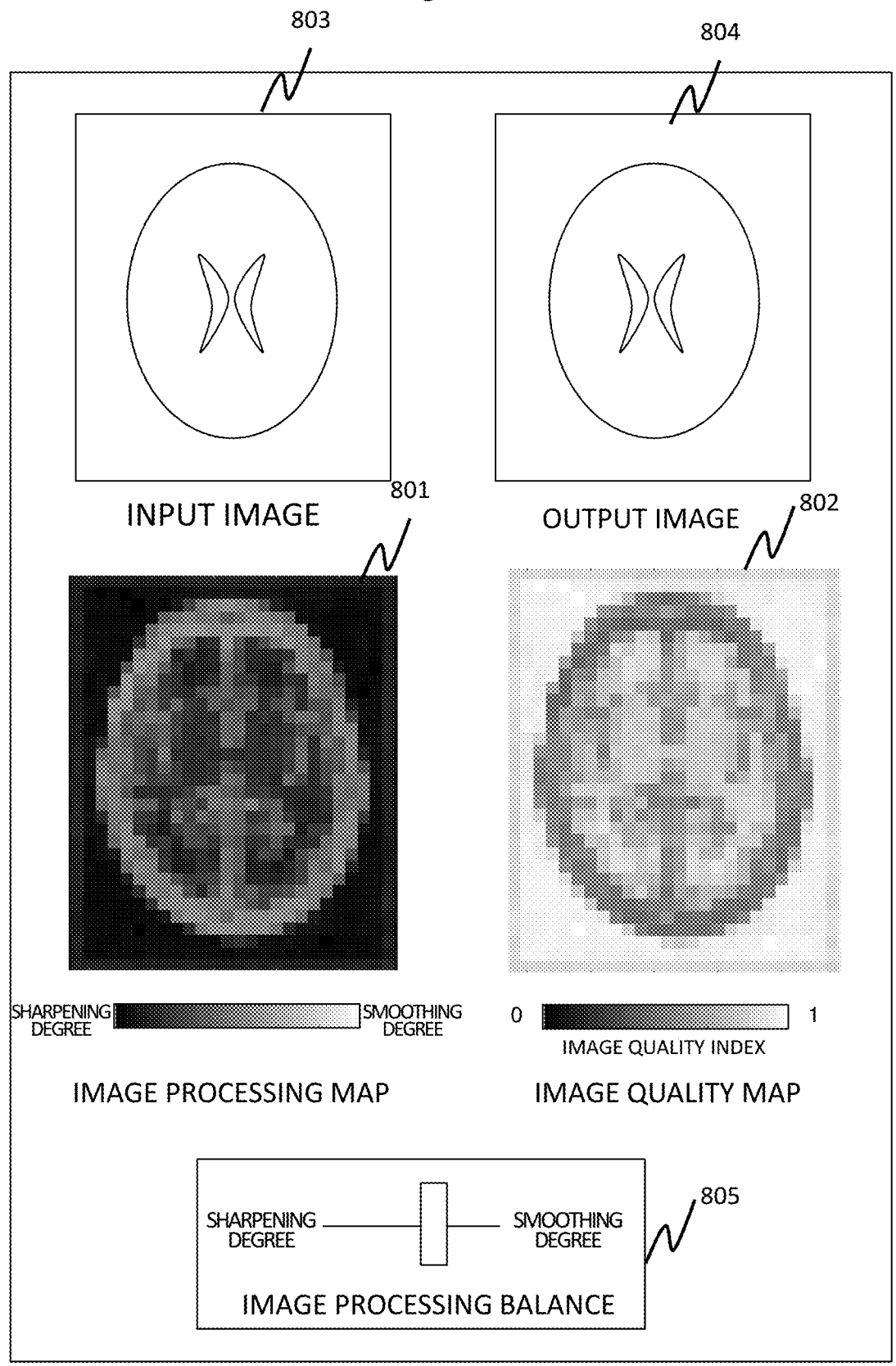
FIG. 8 is a reference drawing illustrating another example in which medical images before and after being subjected to noise reduction in the image processor depicted in FIG. 2, and an image processing map and an image quality map are displayed.

FIGS. 7 and 8 illustrate examples of display screens to be displayed on the display 210. In the example illustrated in FIG. 7, an image processing map 701 and an image quality map 702 are displayed. The image processing map 701 is an image in which the processing that the noise reducer 212 carried out is mapped. A user can ascertain the ratios at which sharpening and smoothing were carried out by viewing the image processing map 701. The image quality map 702 is an image in which an index such as the peak SN ratio (PSNR) and the structural similarity (SSIM) is mapped. By viewing the image quality map 702, a user can confirm the portions where the index is good and the portions where the index is not good. Furthermore, when, as discussed later in the modification examples, a plurality of types of learned machine learning models are stored, depending on the index of the image quality map, the noise reduction processing may be carried out again using a different learned machine learning model. This processing may be carried out in accordance with an instruction from a user, or the image processor may determine to carry out the processing on the basis of the index of the image quality map.

In the example illustrated in FIG. 8, a GUI is displayed in which, in addition to an image processing map 801 and an image quality map 802, an input image (before noise reduction) 803, an output image (after noise reduction) 804, and a bar 805 for the user to manually adjust the image processing balance are displayed. By adjusting the image processing balance adjusting bar 805, the user can send, to the image processor 200, an instruction for increasing/decreasing the degree of sharpening or the degree of smoothing more than the currently displayed image processing map 801. The image processor 200 receives this user instruction and, as described later in the modification examples, selects an optimal learning model from the plurality of types of learning models and carries out the processing.

Note that, in FIGS. 7 and 8, examples are illustrated in which both an image processing map and an image quality map are displayed, but configurations are possible in which only one of these maps is displayed.

As described above, according to the present embodiment, a machine learning model is used that is obtained by learning using a plurality of sets consisting of images with noise and images without noise. As a result, noise reduction effects can be improved and medical images with high image quality can be acquired. In addition, the filter layer of an early stage (the first layer) of the convolution layers of the machine learning model does not consist of filters automatically generated by machine learning, but rather is a layer with known characteristics that includes a plurality of linear or nonlinear filters for which the convolution coefficients are predetermined. As such, it is easy to analyze the content of the noise reduction processing. For example, it is possible to analyze the processing content and discern that, for example, the smoothing filter and the sharpening filter are being respectively applied at ratios of 0.7 and 0.3. These analysis results may be displayed on the display 201.

Accordingly, even when the noise reduction is based on an incorrect determination, it is easy to analyze the processing content and, as such, it is possible to ascertain whether the determination is incorrect, and highly accurate noise reduction processing can be carried out. In particular, the content of the noise reduction processing can be visually provided to the user by displaying the image processing map and the image quality map together with the image after noise reduction.

Modification Examples

Figure 9:
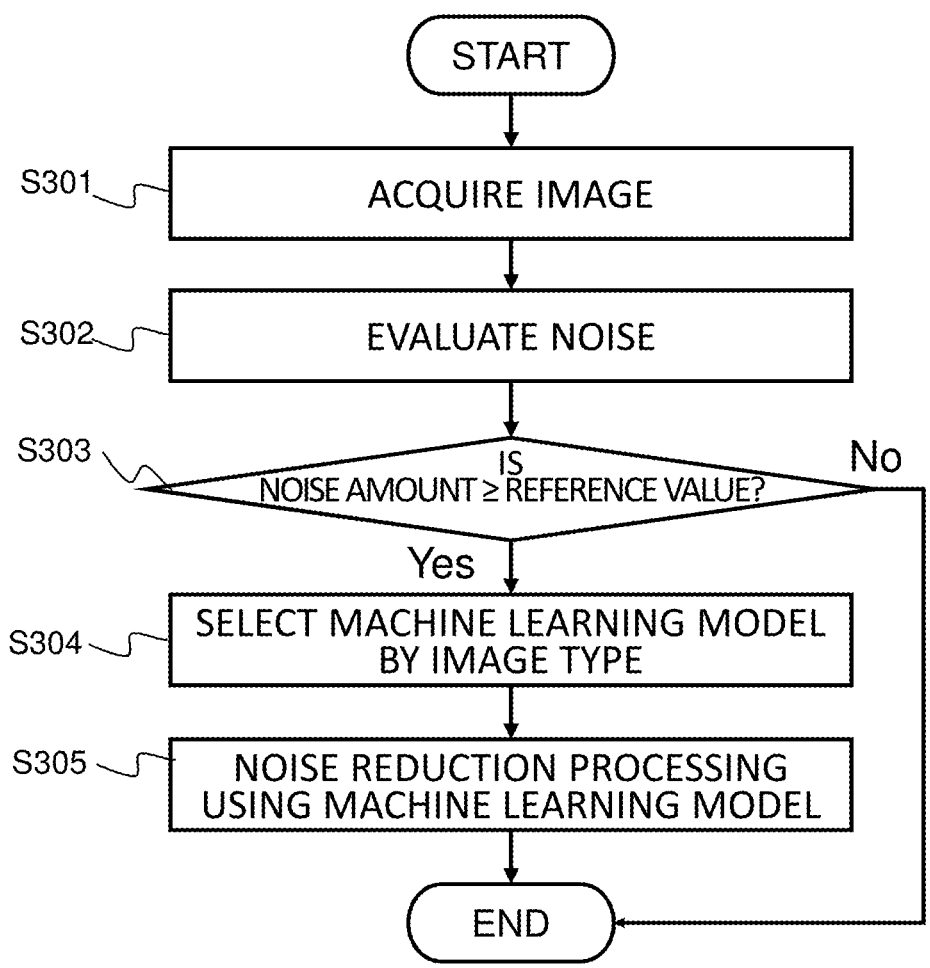
FIG. 9 is a flowchart explaining the noise reduction processing according to a modification example of Embodiment 1.

A configuration is possible in which a plurality of machine learning models is prepared according to the type, the body part, the imaging conditions, and the like of the medical image to be subjected to the noise reduction processing and, when carrying out the noise reduction processing, an optimal machine learning model is selected. In this case, processing is carried out in accordance with the flowchart illustrated in FIG. 9.

Specifically, in step S301, the image processor 200 acquires a medical image using the image acquirer 202. Next, in step S302, the noise level of the acquired medical image is evaluated.

In step S303, the noise level evaluated in step S302 is compared with the reference value stored in the storage device 103, and it is determined whether the noise level of the medical image exceeds the reference value. In the determination in step S303, when the noise level of the medical image exceeds the reference value, step S304 is executed. In step S304, the additional information (information such as the type, the body part, and the imaging conditions of the image) of the medical image stored in the storage device 203 is used to select a machine learning model that is optimal for the medical image that is linked to that information. Alternatively, a configuration is possible in which the user inputs the information required to select an optimal machine learning model, and the optimal machine learning model is selected on the basis of that user input. For example, when, as illustrated in FIG. 8, a processing balance instruction is received via a user operation of the image processing balance adjusting bar 805, a machine learning model is selected that carries out processing at the instructed processing balance.

Then, as in the embodiment described above, in step S305, the noise reduction processing is carried out using the selected machine learning model. In the determination in step S303, when the noise level of the medical image is less than the reference value, the processing is ended without carrying out the noise reduction processing.

The image data to be processed may be spatial three-dimensional volume data, or may be four-dimensional data that also includes a time axis direction. The image data may be absolute value data, phase data, or complex data. In addition to images in which tissue structure is visualized such as a T1-weighted image or a T2-weighted image, the processing may also be applied to images in which blood flow is visualized such as an MRA, and images in which a quantitative value such as the diffusion coefficient is visualized.

According to the nuclear magnetic resonance imaging apparatus of the present embodiment, it is possible to acquire a low-noise image with a large number of samplings from a high-noise image that was acquired with a low number of samplings. As such, it is possible to shorten the imaging time, for example.

Embodiment 2

Next, an embodiment in which the present invention is applied to an ultrasonic imaging apparatus is described.

Figure 10:
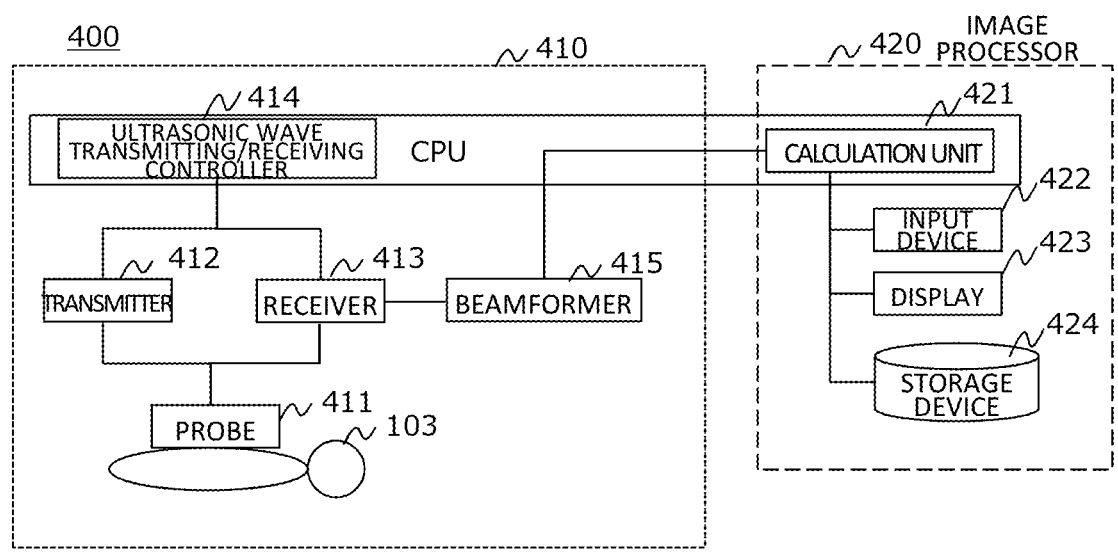
FIG. 10 is a drawing illustrating an overview of a medical imaging apparatus (an ultrasonic imaging apparatus) according to Embodiment 2.

FIG. 10 illustrates an overview of an ultrasonic imaging apparatus 400. This apparatus includes an ultrasonic imaging device 410, and an image processor 420 that carries out calculations for image reconstruction and the like using ultrasonic signals received from the ultrasonic imaging device 410.

The ultrasonic imaging device 410 has the same configuration as a conventional ultrasonic imaging apparatus. The ultrasonic imaging device 410 includes an ultrasonic probe 411 that emits ultrasonic waves, a transmitter 412 that transmits ultrasonic drive signals to the probe 411, an ultrasonic wave receiver 413 that receives ultrasonic signals (RF signals) from the probe 411, a beamformer 415 that beam forms the signals received by the ultrasonic wave receiver 413, and an ultrasonic wave transmitting/receiving controller 414 that controls the ultrasonic waves transmitter 412 and the ultrasonic wave receiver 413.

The image processor 420 includes a calculation unit 421 that generates an ultrasonic image from the ultrasonic signals acquired by the imaging device 410 and carries out the same processing as the calculation unit 201 of the image processor 200 of Embodiment 1, an input device 422, a display 423, and a storage device 424. The calculation unit 421 may further include a Doppler processor or the like (not illustrated in the drawings). In the configuration example illustrated in FIG. 10, the ultrasonic wave transmitting/receiving controller 414 and the calculation unit 421 are provided in a single CPU. However, configurations are possible in which the ultrasonic wave transmitting/receiving controller 414 is provided in a different CPU than the calculation unit 421, and in which the ultrasonic wave transmitting/receiving controller 414 is implemented as a combination of hardware such as a transmitting/receiving circuit and control software.

The configuration and functions of the calculation unit 421 are the same as the calculation unit 201 of Embodiment 1 and, as illustrated in FIG. 2, the calculation unit 421 includes the noise evaluator 211, the noise reducer 212, and the image quality evaluator 213. A configuration is possible in which the noise evaluator 211 and the image quality evaluator 213 are omitted.

Ultrasonic images with differing image quality (for example, B-mode images) are prepared as the learning data for constructing the learning model to be used by the noise reducer 212 of the present embodiment. One example thereof is a combination of an image that achieved high resolution by reducing the frame rate and an image captured at a high frame rate. A learning model is constructed in the same manner (the flowchart illustrated in FIG. 4) as in Embodiment 1 using this learning data. This learning model also is a learning model that includes a plurality of layers and, as illustrated in FIG. 5, the first layer is a filter layer in which a plurality of predetermined linear or nonlinear filters are incorporated.

A plurality of such learning models can be prepared in accordance with the type, the body part, the imaging conditions, and the like of the ultrasonic image.

In the imaging, the ultrasonic imaging device 410 beam forms the ultrasonic waves received by the probe 411, and sends an ultrasonic signal to the image processor 420. The image processor 420 carries out processing that is the same as in Embodiment 1. First, an ultrasonic image is generated from the ultrasonic signal, and the noise of the generated ultrasonic image is evaluated by the noise evaluator 211. If the noise is less than or equal to a reference value stored in advance in the storage device 424, the ultrasonic image is displayed on the display 423 without carrying out the noise reduction processing. When the noise of the ultrasonic image exceeds the reference value, the noise reducer 212 carries out the noise reduction processing using the learning model described above. Specifically, the original image is used as the input and an image with reduced noise is output. In this case, when a plurality of learning models is prepared in advance, the optimal learning model is selected according to the purpose of the imaging and the noise reduction processing is carried out.

The image quality evaluator 213 may also evaluate the image quality of the image after the noise reduction processing, and create an image (image processing map and/or image quality map) that expresses the processing results. The option of displaying the image that expresses the processing results on the display 423 and the option of receiving a user instruction on the display screen about the processing balance are the same as in Embodiment 1.

According to the ultrasonic imaging apparatus of the present embodiment, it is possible to acquire a low-noise image with a large number of samplings from a high-noise image that was acquired with a low number of samplings. As such, it is possible to perform high frame rate imaging, for example.

Embodiment 3

Next, an embodiment in which the present invention is applied to a CT apparatus is described.

Figure 11:
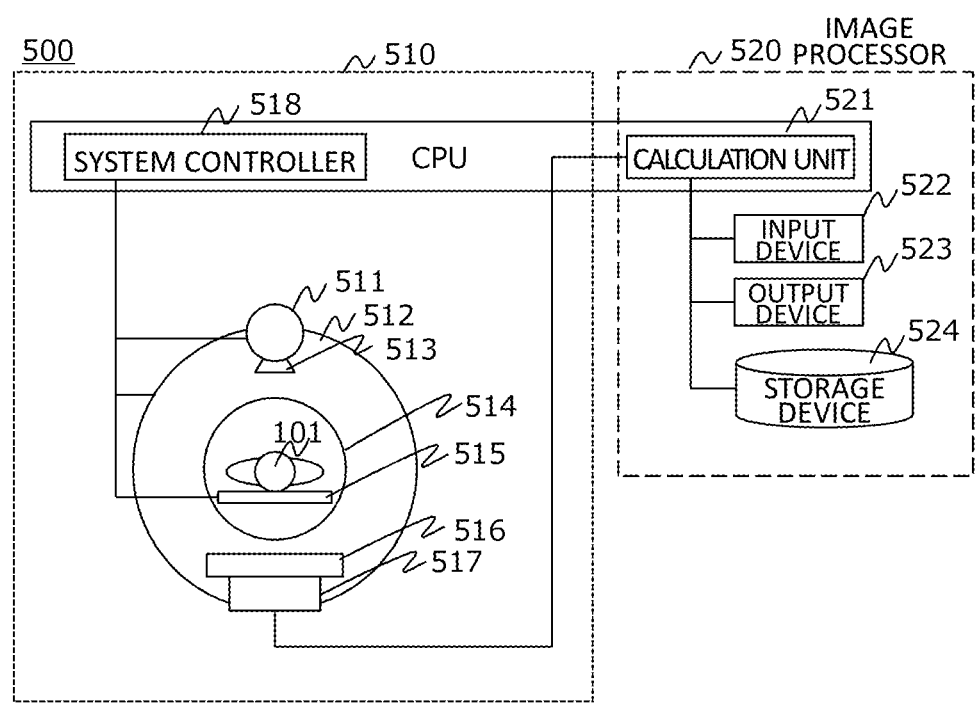
FIG. 11 is a drawing illustrating an overview of a medical imaging apparatus (a CT apparatus) according to Embodiment 3.

FIG. 11 illustrates an overview of a CT apparatus 500. This device roughly includes a CT imaging device 510, and an image processor 520 that carries out calculations for image reconstruction and the like using CT image signals received from the CT imaging device 510.

The CT imaging device 510 has the same configuration as a conventional CT apparatus. The CT imaging device 510 includes an X-ray source 511 that irradiates X-rays on a subject 103, a collimator 513 that restricts the irradiation range of the X-rays, an X-ray detector 516 that detects transmitted X-rays that have transmitted through the subject 103, a rotating plate 512 that includes an opening 514 at the center thereof and supports the X-ray source 511 and the X-ray detector 516 at opposing positions, a table 515 in the space inside the opening 514 on which the subject 103 is placed, a data collector 517 that collects the output of the X-ray detector 516 for each piece of projection data, and a system controller 518 that controls the operations of the various components of the CT imaging device 510.

The image processor 520 includes a calculation unit 521 that carries out the same processing as the calculation unit 201 of Embodiment 1 on a tomographic image (CT image) generated by the imaging device 510, an input device 522, a display (output device) 523, and a storage device 524. In the configuration example illustrated in FIG. 11, the system controller 518 and the calculation unit 521 are provided in a single CPU. However, configurations are possible in which the system controller 518 is provided in a different CPU than the calculation unit 521, and in which the system controller 518 is implemented as a combination of hardware and control software. Likewise, a portion of the functions of the image processor 520 may be implemented as hardware.

The functions of the calculation unit 521 are the same as the functions of the calculation unit 201 the image processor 200 of Embodiment 1 and, as illustrated in FIG. 2, the calculation unit 521 includes the noise evaluator 211, the noise reducer 212, and the image quality evaluator 213.

CT images with differing image quality are prepared as the learning data for constructing the learning model to be used by the noise reducer 212 of the present embodiment. One example thereof is a combination of a high resolution image acquired at high-dose and low resolution image acquired at low-dose. The learning model is constructed in the same manner (the flowchart illustrated in FIG. 4) as in Embodiment 1 using such learning data. This learning model also is a learning model that includes a plurality of layers and, as illustrated in FIG. 5, the first layer is a filter layer in which a plurality of predetermined linear or nonlinear filters are incorporated.

A plurality of such learning models can be prepared in accordance with the imaged part, the imaging conditions, and the like.

In the imaging, X-ray signals of the transmitted X-rays detected by the X-ray detector 516 in the CT imaging device 510 are collected by the data collector 517 and transmitted to the image processor 520. As in Embodiment 1, first, the image reconstructer of the image processor 520 generates a CT image. Then, the generated CT image is subjected to the same processing as described in Embodiment 1. First, the noise of the generated CT image is evaluated by the noise evaluator 211. If the noise is less than or equal to a reference value stored in advance in the storage device 524, the CT image is displayed on the display 523 without carrying out the noise reduction processing. When the noise of the CT image exceeds the reference value, the noise reducer 212 carries out the noise reduction processing using the learning model described above. Specifically, the original image is used as the input and an image with reduced noise is output. In this case, when a plurality of learning models is prepared in advance, the optimal learning model is selected according to the purpose of the imaging and the noise reduction processing is carried out.

In addition, the image quality evaluator 213 may evaluate the image quality of the image after the noise reduction processing, and create an image (image processing map and/or image quality map) that expresses the processing results. The option of displaying the image that expresses the processing results on the display 523 and the option of receiving a user instruction on the display screen about the processing balance are the same as in Embodiment 1 and Embodiment 2.

According to the CT apparatus of the present embodiment, it is possible to acquire a low-noise image, which is acquirable at high-dose, from a high-noise image that was acquired at low-dose. As such, it is possible to perform a highly accurate diagnosis using imaging that requires low exposure.

Various embodiments of the medical imaging device of the present invention and the image processor thereof have been described but, as described above, the image processor of each of the imaging devices may be configured as an image processing device that is independent from the imaging device.

What is claimed is:

1. A medical imaging apparatus, comprising:
   an imaging device that acquires a medical image; and
   an image processor, coupled to a display, configured to carry out convolution processing on the medical image;
   wherein the image processor includes:
      a storage unit that stores a plurality of filters each having corresponding predetermined convolution coefficients and a weighting factor of each of the sets of convolution coefficients, and
      a calculation unit configured to:
      carry out calculation of the convolution processing using the plurality of filters and the corresponding convolution coefficients and the weighting factors thereof that are stored in the storage unit, and
      thereafter, generate an image processing map indicating a ratio among two of the plurality of filters used in combination in the convolution processing,
   wherein image quality is improved by the convolution processing, and
   wherein the image processing map is displayed on the display.

2. The medical imaging apparatus according to claim 1, wherein the convolution coefficients are calculated by a learning model that includes the plurality of layers, the learning model being learned on the basis of a data set that includes a high-noise image as input data and a low-noise image as output data.

3. The medical imaging apparatus according to claim 2, wherein one layer of the learning model includes a filter layer in which a plurality of predetermined linear or nonlinear filters is incorporated.

4. The medical imaging apparatus according to claim 3, wherein the filter layer is a first layer.

5. The medical imaging apparatus according to claim 2, wherein:
   the image processor includes:
      a noise evaluator that evaluates whether noise in the medical image exceeds a predetermined reference value, and
      a noise reducer that reduces the noise of the medical image that has been determined, by the noise evaluator, to include noise that exceeds the reference value, wherein
   the noise reducer reduces the noise of the medical image using the learning model.

6. The medical imaging apparatus according to claim 5, further comprising:
   an image quality evaluator that evaluates the medical image subjected to noise reduction processing by the noise reducer, wherein
   the image quality evaluator generates an image quality map in which an image quality evaluation index is mapped.

7. The medical imaging apparatus according to claim 6, wherein:
   the storage unit includes a plurality of learning models learned on the basis of a plurality of types of image learning data sets, and
   the image quality evaluator selects an appropriate learning model from the plurality of learning models using at least one of the image processing map and the image quality map, and the noise reducer applies the learning model that is selected and carries out the noise reduction processing.

8. The medical imaging apparatus according to claim 6, wherein:
   the storage unit includes a plurality of learning models learned on the basis of a plurality of types of image learning data sets, and
   the image quality map is displayed on the display, and an adjuster that receives, via the display, an adjustment of an image processing balance by a user, wherein
   the noise reducer selects, in accordance with the adjustment by the user, an appropriate learning model from the plurality of learning models, applies the learning model that is selected, and carries out the noise reduction processing.

9. The medical imaging apparatus according to claim 1, wherein the medical image is three-dimensional volume data.

10. The medical imaging apparatus according to claim 1, wherein:
    the medical imaging apparatus is a nuclear magnetic resonance imaging apparatus, and
    the image processor carries out image reconstruction using k space data acquired by the nuclear magnetic resonance imaging apparatus.

11. The medical imaging apparatus according to claim 10, wherein the storage unit includes a plurality of sets of convolution coefficients calculated by a learning model that includes a plurality of layers, the learning model being learned on the basis of a data set that includes a high-noise image acquired by undersampling as input data and a low-noise image that is full sampled as output data.

12. A medical image processing device, comprising:
    a medical image acquirer that acquires a medical image;
    an image processor, coupled to a display, configured to carry out convolution processing on the medical image; and
    a storage unit that stores a plurality of filters each having corresponding predetermined convolution coefficients and a weighting factor of each of the sets of convolution coefficients;
    wherein the plurality of sets of convolution coefficients are calculated by a learning model that includes the plurality of layers, the learning model being learned on the basis of a data set that includes a high-noise image as input data and a low-noise image as output data,
    wherein one layer of the learning model includes a filter layer in which a plurality of predetermined linear or nonlinear filters is incorporated, wherein image quality is improved by convolution processing of the plurality of sets of convolution coefficients stored in the storage unit, wherein the image processor generates an image processing map indicating a ratio among two of the plurality of filters used in combination in the convolution processing, and wherein the image processing map is displayed on the display.

\* \* \* \* \*